(12) United States Patent
Long

(10) Patent No.: US 7,232,438 B2
(45) Date of Patent: Jun. 19, 2007

(54) ABLATION DEVICE WITH CLEAR PROBE

(75) Inventor: Gary L. Long, Cincinnati, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 0 days.

(21) Appl. No.: 10/887,646

(22) Filed: Jul. 9, 2004

(65) Prior Publication Data

US 2006/0009757 A1 Jan. 12, 2006

(51) Int. Cl.
*A61B 18/14* (2006.01)

(52) U.S. Cl. .......................................................... 606/41

(58) Field of Classification Search ................. 600/114, 600/129; 606/41
See application file for complete search history.

(56) References Cited

U.S. PATENT DOCUMENTS

| | | | |
|---|---|---|---|
| 874,810 A | 12/1907 | Wappler | |
| 4,202,336 A | 5/1980 | Van Gerven | |
| 4,237,871 A | 12/1980 | Bonnet | |
| 4,532,924 A | 8/1985 | Auth et al. | |
| 4,582,057 A | 4/1986 | Auth et al. | |
| 4,646,722 A | 3/1987 | Silverstein et al. | |
| 4,765,331 A | 8/1988 | Petruzzi et al. | |
| 4,807,593 A | 2/1989 | Ito | |
| 4,819,620 A | 4/1989 | Okutsu | |
| 5,025,778 A | 6/1991 | Silverstein et al. | |
| 5,080,660 A | 1/1992 | Buelna | |
| 5,112,308 A | 5/1992 | Olsen et al. | |
| 5,122,138 A | 6/1992 | Manwaring | |
| 5,156,151 A | 10/1992 | Imran | |
| 5,336,222 A | 8/1994 | Durgin, Jr. et al. | |
| 5,395,327 A | 3/1995 | Lundquist et al. | |
| 5,500,012 A | 3/1996 | Brucker et al. | |
| 5,681,282 A | 10/1997 | Eggers et al. | |
| 5,695,448 A | 12/1997 | Kimura et al. | |
| 5,697,882 A | 12/1997 | Eggers et al. | |
| 5,697,909 A | 12/1997 | Eggers et al. | |
| 5,746,696 A | 5/1998 | Kondo | |

(Continued)

FOREIGN PATENT DOCUMENTS

JP 01/079017 10/1999

(Continued)

OTHER PUBLICATIONS

Guiterrez, Jorge G., et al., A Multipurpose Overtube for Diagnostic and Therapeutic Flexible Fiberoptic Endoscopy. *Gastrointestinal Endoscopy*, 1986, 32(4):274-277.

(Continued)

*Primary Examiner*—Lee S. Cohen
(74) *Attorney, Agent, or Firm*—Victor C. Moreno

(57) ABSTRACT

A medical device for performing a therapeutic procedure on a patient. The medical device includes an elongate probe extending to an applicator end and a visually transparent tip positioned adjacent the applicator end. The device also includes an electrode positioned on the tip so that the electrode may be viewed through the tip. The electrode is communicative with an energy source for delivering energy to the electrode when performing the therapeutic procedure on the patient. The probe and tip are sized and shaped to be slidably received in an endoscope working channel.

20 Claims, 2 Drawing Sheets

U.S. PATENT DOCUMENTS

| | | | |
|---|---|---|---|
| 5,749,889 A | 5/1998 | Bacich et al. | |
| 5,766,152 A | 6/1998 | Morley et al. | |
| 5,766,153 A | 6/1998 | Eggers et al. | |
| 5,782,760 A | 7/1998 | Schaer | |
| 5,782,824 A | 7/1998 | Abela | |
| 5,789,047 A | 8/1998 | Sasaki et al. | |
| 5,846,182 A | 12/1998 | Wolcott | |
| 5,871,481 A * | 2/1999 | Kannenberg et al. | 606/34 |
| 5,873,877 A | 2/1999 | McGaffigan et al. | |
| 5,888,198 A | 3/1999 | Eggers et al. | |
| 5,902,272 A | 5/1999 | Eggers et al. | |
| 5,941,834 A | 8/1999 | Skladnev | |
| 5,961,526 A | 10/1999 | Chu et al. | |
| 6,009,877 A | 1/2000 | Edwards | |
| 6,010,450 A | 1/2000 | Perkins | |
| 6,022,334 A | 2/2000 | Edwards et al. | |
| 6,027,499 A | 2/2000 | Johnston | |
| 6,056,744 A | 5/2000 | Edwards | |
| 6,066,134 A | 5/2000 | Eggers et al. | |
| 6,068,603 A | 5/2000 | Suzuki | |
| 6,071,233 A | 6/2000 | Ishikawa et al. | |
| 6,086,583 A * | 7/2000 | Ouchi | 606/41 |
| 6,091,993 A | 7/2000 | Bouchier et al. | |
| 6,091,995 A | 7/2000 | Ingle et al. | |
| 6,106,521 A | 8/2000 | Blewett et al. | |
| 6,120,434 A | 9/2000 | Kimura et al. | |
| 6,142,931 A | 11/2000 | Kaji | |
| 6,146,378 A | 11/2000 | Mikus et al. | |
| 6,149,620 A | 11/2000 | Baker et al. | |
| 6,179,832 B1 | 1/2001 | Jones et al. | |
| 6,190,381 B1 | 2/2001 | Olsen et al. | |
| 6,210,410 B1 * | 4/2001 | Farin et al. | 606/49 |
| 6,235,020 B1 | 5/2001 | Cheng et al. | |
| 6,238,389 B1 | 5/2001 | Paddock et al. | |
| 6,241,702 B1 | 6/2001 | Lundquist et al. | |
| 6,241,724 B1 | 6/2001 | Fleischman et al. | |
| 6,254,598 B1 | 7/2001 | Edwards et al. | |
| 6,258,087 B1 | 7/2001 | Edwards et al. | |
| 6,296,638 B1 | 10/2001 | Davison et al. | |
| 6,309,379 B1 | 10/2001 | Willard et al. | |
| 6,325,798 B1 | 12/2001 | Edwards et al. | |
| 6,346,108 B1 * | 2/2002 | Fischer | 606/49 |
| 6,355,034 B2 | 3/2002 | Cosmescu | |
| 6,394,949 B1 | 5/2002 | Crowley | |
| 6,402,742 B1 | 6/2002 | Blewett et al. | |
| 6,405,732 B1 | 6/2002 | Edwards et al. | |
| 6,524,251 B2 * | 2/2003 | Rabiner et al. | 600/439 |
| 6,551,310 B1 | 4/2003 | Ganz et al. | |
| 6,645,201 B1 | 11/2003 | Utley et al. | |
| 6,740,082 B2 | 5/2004 | Shadduck | |
| 2002/0147447 A1 | 10/2002 | Long | |
| 2002/0156470 A1 | 10/2002 | Shadduck | |
| 2002/0177847 A1 | 11/2002 | Long | |
| 2002/0183739 A1 | 12/2002 | Long | |
| 2003/0009162 A1 | 1/2003 | Messing et al. | |
| 2003/0009163 A1 | 1/2003 | Messing et al. | |
| 2003/0181905 A1 | 9/2003 | Long | |
| 2003/0216727 A1 | 11/2003 | Long | |
| 2004/0054366 A1 * | 3/2004 | Davison et al. | 606/39 |

FOREIGN PATENT DOCUMENTS

| | | |
|---|---|---|
| WO | WO 01/35846 A1 | 5/1991 |
| WO | WO 99/00060 | 1/1999 |
| WO | WO 99/35986 | 7/1999 |
| WO | WO 00/18314 | 4/2000 |
| WO | WO 00/19926 A1 | 4/2000 |
| WO | WO 00/35364 | 6/2000 |
| WO | WO 01/05318 A1 | 1/2001 |
| WO | WO 01/24721 A1 | 4/2001 |
| WO | WO 02/47569 A1 | 6/2002 |

OTHER PUBLICATIONS

Rogers, B.H. Gerald, et al., An Overtube for the Flexible Fiberoptic Esophagogastroduodenscope. *Gastrointestinal Endoscopy*, 1982, 28(4): 256-57.

EPO Search Report dated Jul. 26, 2004 for related European Patent Application No. EP 04 25 1414.

EPO Search Report dated Apr. 22, 2005 for related patent application. European Patent Application No. EP 03 255 823.1.

* cited by examiner

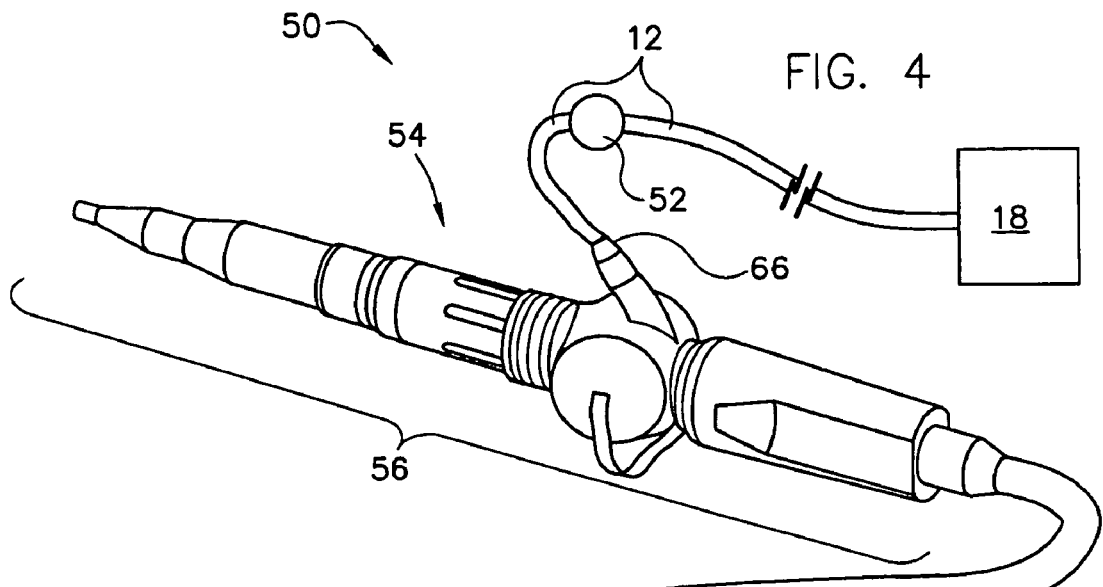
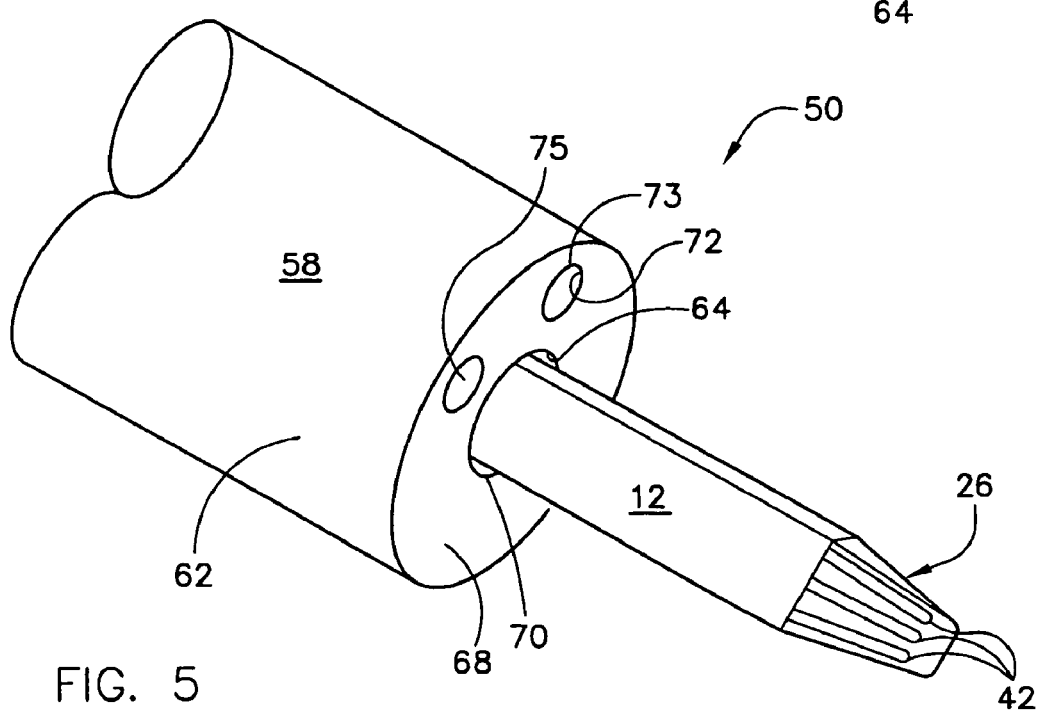

ABLATION DEVICE WITH CLEAR PROBE

FIELD OF INVENTION

The present invention relates to a medical device, and more particularly to an ablation device having a clear probe and methods for performing a therapeutic procedure on a patient therewith.

BACKGROUND OF THE INVENTION

Various devices and methods have been traditionally used to combat a physical condition known as Barrett's esophagus. Barrett's esophagus is the abnormal growth of intestinal type cells into the esophagus resulting from stomach acid chronically refluxing into the esophagus. Most people occasionally experience heartburn, which is the refluxing of stomach acid beyond the lower esophageal sphincter muscle and into the esophagus.

Such occasional heartburn is not harmful. Severe or frequent reflux, however, is harmful and known by the names gastroesophageal reflux disease (GERD) and chronic reflux esophagitis (also known as Chronic Acid Reflux, or CAR). About one out of every ten patients with GERD/CAR are found to have Barrett's esophagus. In patients with Barrett's esophagus, the healthy mucosal cells of the inner layer or the squamous epithelium of the esophagus are replaced with diseased or intestinal cells. It is believed that such growth is a defense mechanism of the body to avoid esophageal injury due to the acid refluxed from the stomach. Unfortunately, these mucosal tissue changes may lead to low, then high grade dysplasia, and eventually to cancer of the lower esophagus, known as adenocarcinoma.

A common method for destroying diseased esophageal tissue has been to cauterize or coagulate the unwanted tissue with a conventional ablation device. Ablation devices have developed as an alternative to other traditional means of eliminating unwanted tissue, such as cutting away the tissue, cryotherapy, and thermal therapy. Cryotherapy is the application of extreme cold to freeze and destroy diseased mucosal tissue. Thermal therapy is the application of heat to coagulate, cauterize and/or ablate diseased mucosal tissue. Sufficient raising or lowering of tissue temperature causes necrosis of the tissue. For convenience, the term ablate will be used herein to describe any and all of these thermal therapy processes. In use, these devices are placed adjacent the unwanted tissue and tissue is ablated, cauterized, coagulated, frozen, or burnt, as the case may be, by energy transmitted from or to the device.

Traditional ablation devices are used in conjunction with an endoscope. Most of these traditional devices are either a capping type or an insertion type. Capping type ablation devices fit over and around the end of the tubular portion of the endoscope. Such capping type ablation devices are often visually transparent to allow the user to see through them when they are viewed with the endoscope optics. Shortcomings of capping type devices include their large size, poor maneuverability, inaccuracy, complexity, and need to be and stay secured. Regarding their large size, at least a portion of capping type ablation devices is necessarily wider than the working end of the endoscope because such devices attach to endoscopes by fitting over and around the working end of the endoscope. Larger size, among other things, results in a more invasive procedure. Further, movement of capping type devices is limited to the movement of the endoscope. That is, normally there is no relative motion between a capping type ablation device and the endoscope with which it is used. The inaccuracy of capping type devices primarily results from the size and maneuverability. For instance, when targeting particular tissue, the larger size and lack of maneuverability lowers the likelihood that targeted tissue, and no other tissue, will be ablated. Further, capping devices require structure to attach the device to the endoscope. This attachment structure adds complexity to the device compared with devices not requiring such structure. In addition, such attachment structure is usually required to be selectively removable from the endoscope and there is the potential for the device to become displaced or completely disconnected from the endoscope during the procedure. Attachment structure designed to greatly lower the likelihood of unintentional disconnection would further increase the complexity and size of the device.

The other type of conventional ablation device, the insertion type, is inserted into the working channel of the endoscope. Traditional insertion type devices have opaque probes for ablating tissue. The probes contain the energy transferring devices with which the unwanted tissue is destroyed. A primary shortcoming of insertion type devices is the inability to view through the probes. This inability results in maneuvering difficulties and reduced accuracy in use. For instance, because the probe is not visually transparent, a user must estimate the position of the probe when positioning of the device within the patient and during the energy transmitting procedure. The requirement to estimate the position of the device during the energy transmission prevents the user from knowing whether the energy transmission has affected the targeted tissue until the tissue visible around the opaque tip has been affected. The likelihood of destroying healthy cells is greatly increased when such delayed and indirect feedback is used.

A primary challenge for battling Barrett's esophagus is to destroy targeted tissue without affecting healthy adjacent esophageal cells or muscular cells underlying the diseased and healthy tissue. Injury to the healthy underlying muscular tissue, for example, can lead to the creation of a stricture or constriction in the esophagus. Another challenge is to have a device that is relatively simple and easy to use. The conventional approaches to treating Barrett's esophagus, or other diseases requiring the precise and relatively easy ablation of tissue, are insufficient in these regards. Thus, there is a need for an ablation device and method for using such a device that are accurate, minimally invasive, and relatively easy to maneuver and operate.

BRIEF SUMMARY OF THE INVENTION

The present invention includes a medical device for performing a therapeutic procedure on a patient. The medical device includes an elongate probe extending to an applicator end and a visually transparent tip positioned adjacent the applicator end. The device also includes an electrode positioned on the tip so that the electrode may be viewed through the tip. The electrode is communicative with an energy source for delivering energy to the electrode. The probe and tip are sized and shaped to be slidably received in an endoscope working channel.

In another aspect, the present invention includes a medical device for performing a therapeutic procedure on a patient. The device comprises an elongate endoscope extending to a working end. The endoscope includes optics for viewing an object positioned in a viewing area adjacent the working end of the endoscope and having a working channel extending along the endoscope to a port adjacent the working end. The device also includes an elongate probe slidably received in the working channel of the endoscope. The probe includes a visually transparent tip positionable adjacent the working end of the endoscope and in the viewing area The probe further includes an electrode positioned on the tip so that the electrode may be viewed through the optics of the endoscope when the tip is positioned adjacent the working end of the endoscope and in the viewing area. The electrode is communicative with an energy source for delivering energy to the electrode when performing the therapeutic procedure on the patient.

In yet another aspect, the present invention includes a method for performing a procedure on a patient. The method comprises positioning an elongate probe in a working channel of an endoscope so a transparent tip connected to the probe having an electrode thereon extends beyond a port at a working end of the endoscope. The method further includes viewing the electrode of the probe through the tip using the endoscope, moving the probe so the electrode is at a desired location within the patient, and energizing the electrode to remove from the patient tissue positioned adjacent the electrode.

Other aspects of the present invention will be in part apparent and in part pointed out hereinafter.

BRIEF DESCRIPTION OF THE FIGURES

FIG. 4 is a perspective view of the device in combination with a conventional endoscope.

FIG. 5 is a detail perspective view of a portion of the combination shown in FIG. 4.

Corresponding reference characters indicate corresponding parts throughout the several views of the drawings.

DETAILED DESCRIPTION OF THE INVENTION

Figure 1:
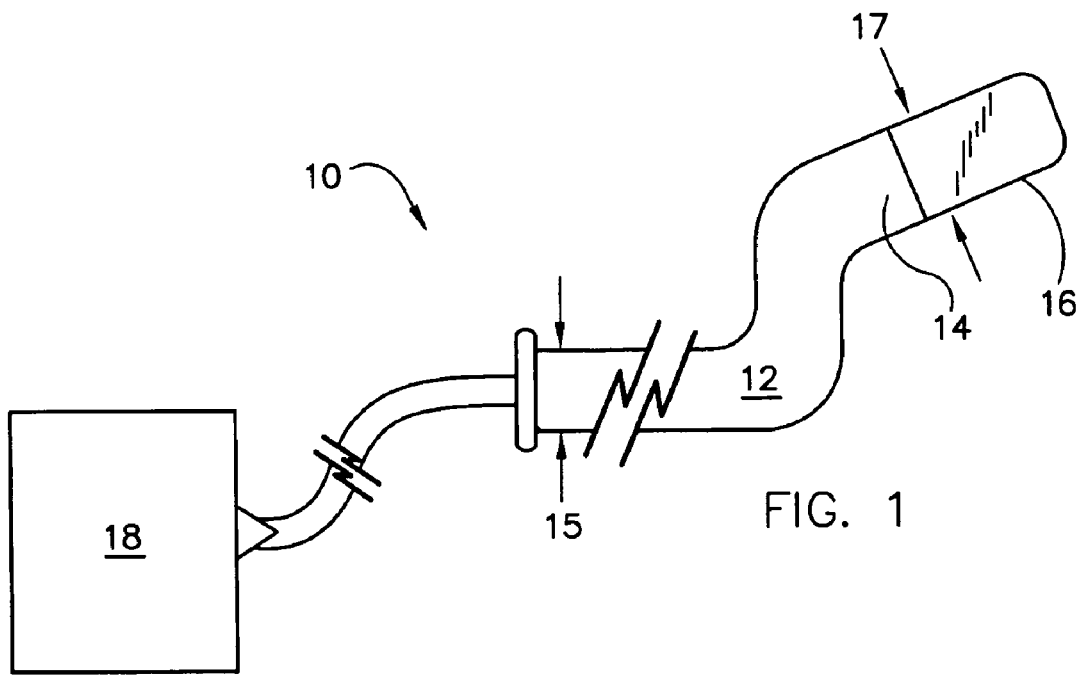
FIG. 1 is a schematic plan view of a first embodiment of a medical device according to the present invention.

The present invention relates to a medical device for performing a therapeutic procedure on a patient, and more particularly a device for ablating tissue within a patient. Referring now to the figures, and more particularly to FIG. 1, a medical device according to a first embodiment of the present invention is designated in its entirety by reference number 10. The medical device 10 has an elongate probe 12 extending to an applicator end 14. Although the probe may be made of other materials without departing from the scope of the present invention, in one embodiment the probe is made of a flexible and thermally and/or electrically insulating material, such as silicone, polyethylene, or polypropylene. Although the probe 12 may have other shapes without departing from the scope of the invention, in one embodiment the probe 12 is generally tubular. Further, although the probe 12 may have other dimensions without departing from the scope of the present invention, in one embodiment the probe has a maximum width 15 of between about 1 millimeter and about 5 millimeters. Having a maximum width less than about 3 millimeters allows the probe 12 to fit inside the working channel of a standard endoscope (not shown in FIGS. 1–3).

A visually transparent tip 16 is connected to the probe 12 adjacent the applicator end 14 of the probe 12. Although the tip 16 may have other dimensions without departing from the scope of the present invention, in one embodiment the tip 16 has a maximum width 17 of between about 1 millimeter and about 5 millimeters. Such a maximum width allows the tip 16, along with a similarly sized probe 12, to slidably fit inside the working channel of an endoscope. Also, although the tip 16 may be made of other materials without departing from the scope of the invention, in one embodiment the tip 16 is made of a thermally and/or electrically insulating material, such as silicone, or a silicone based material. The tip 16 may also be made of polyethylene, polypropylene, glass, quartz, or similar materials.

Figure 2:
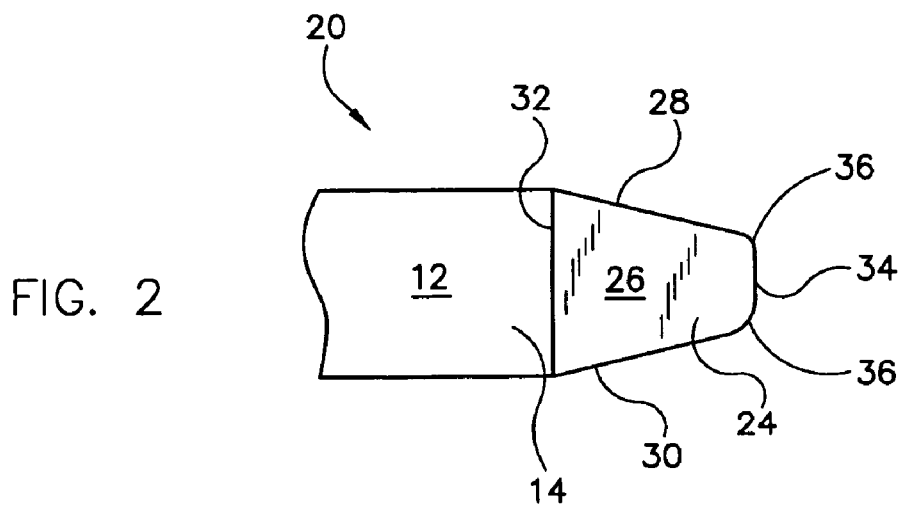
FIG. 2 is a detail plan view of a second embodiment of a medical device according to the present invention.
Figure 3:
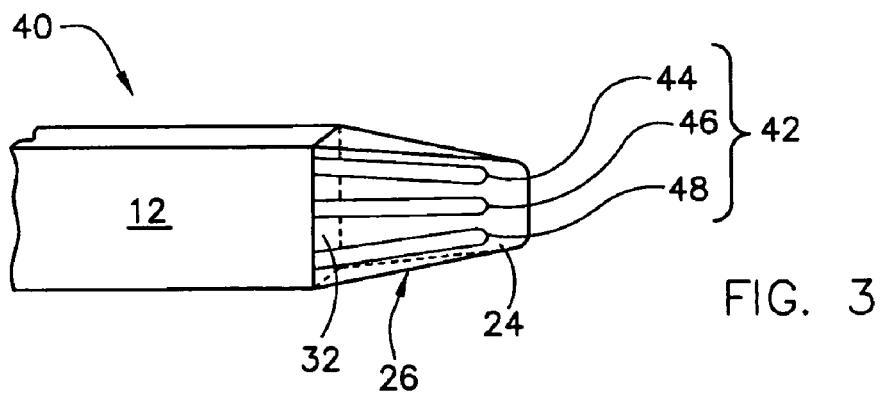
FIG. 3 is a detail perspective view of the medical device.

FIG. 2 shows the applicator end 14 of the probe 12 and a visually transparent tip 26 of an embodiment of a medical device 20 according to the present invention. The tip 26 has a first lateral surface 24 and a second lateral surface (not shown) opposite the first lateral surface. Further in this embodiment, the tip 26 has opposite third and fourth surfaces 28, 30, respectively, separating the first and second lateral surfaces. It will be appreciated from FIG. 2, the third surface 28 and fourth surface 30 taper towards each other from a first end 32 of the tip 26 to a second end 34 of the tip. Similarly, the first lateral surface 24 and the second lateral surface opposite the first surface 24 taper toward one another from the first end 32 to the second end 34 of the tip 26, as can be seen in FIG. 3. Although the tip is shown as non-circular and having sides that taper towards one another, the tip may have other shapes without departing from the scope of the present invention. The tip 26 is preferably shaped to avoid injury. For example, the tip 26 has blunt, rounded edges 36 instead of sharp edges.

FIG. 3 shows a second embodiment of the present invention wherein the medical device 40 has electrodes 42 positioned on the first lateral surface 24 of the tip 28. In this embodiment, the second lateral surface opposite the first surface is substantially free of electrodes. The electrodes 42 may be disposed in other configurations without departing from the scope of the present invention. For example, electrodes may be disposed on both the first and second lateral surfaces. Further, although there are three electrodes 42 shown on the first lateral surface 24, there may be more or fewer electrodes without departing from the scope of the present invention. Similarly, although the electrodes 42 are shown extending from the first end 32 of the tip 26 more than half-way toward the second end 34, the electrodes may extend more or less than half-way between the first end and second end of the tip without departing from the scope of the present invention. Also, although the electrodes 42 are shown extending parallel to each other, the electrodes 42 may be disposed in various orientations and arrangements without departing from the scope of the present invention. For example, adjacent electrodes 42 may get closer together or become increasingly spaced apart as they approach the second end 34, or they may contact and/or cross paths. Although the distance between adjacent electrodes may vary without departing from the scope of the present invention, in one embodiment the electrodes are spaced at least about one-half of a millimeter apart. The electrodes 42 may be made of a stainless steal wire having a diameter of about 0.5 millimeters. The electrodes 42 may have other sizes and be made of other materials without departing from the scope of the present invention.

Because the tip 26 is clear, the electrodes 42 may be viewed through the tip 26 from a position opposite the first lateral surface 24. Although surface 24 may have other shapes without departing from the scope of the present invention, in one embodiment the surface 24 is concave. In one embodiment, the tip 26 magnifies images transmitted from the first lateral surface 24. For example, a user viewing the tip from a position opposite the first lateral surface 24 will see an enlarged view of the electrodes 42 and the tissue adjacent the electrodes (not shown). The magnifying characteristic enhances the accuracy with which the tip 26 can be positioned within the patient and the procedure can be performed. Such accuracy reduces the invasiveness of the procedure and the likelihood of injury due to the procedure.

The electrodes 42 communicate with an energy source 18, as shown in FIG. 1. The energy source 18 delivers energy to the electrodes 42 during use of the medical device 10. Although other energy sources 18 may be used without departing from the scope of the present invention, in one embodiment the energy source 18 is a radio frequency generator for delivering radio frequency energy to the electrodes 42. Although such a radio frequency generator may produce signals with other characteristics without departing from the scope of the present invention, in one embodiment the radio frequency generator produces a signal having an amplitude of between about 20 volts and about 500 volts and a frequency between about 0.3 megahertz and about 1.0 megahertz. In another embodiment, the energy source 18 is an electrical generator for delivering electrical current to the electrodes 42. Although such an electrical generator may produce electrical current having other characteristics without departing from the scope of the present invention, in one embodiment it produces a current having a voltage between about 20 volts and about 500 volts and a frequency between about 0.3 megahertz and about 1.0 megahertz. In still another embodiment, the energy source 18 delivers ultrasonic energy to the electrodes 42. Although such an ultrasonic generator may produce signals with other characteristics without departing from the scope of the present invention, in one embodiment the ultrasonic generator produces a signal having a frequency in the range of about 20 kilohertz to about 100 kilohertz.

In embodiments of the present invention having a plurality of electrodes 42, adjacent electrodes may carry varying charges when the medical device 40 is in use. For example, regarding the radio frequency and electrical power generators 18, adjacent electrodes can be of opposite polarity. For instance, electrode 44 and electrode 48 of the electrodes 42, shown in FIG. 4, can have the same polarity and electrode 46 can have a polarity that is opposite of the polarity of electrodes 44 and 48. Specifically, electrodes 44 and 48 can carry a positive polarity while electrode 46 carries a negative polarity. As an alternative example, electrodes 44 and 48 can carry a negative polarity while electrode 46 carries a positive polarity. Such bipolar energy transmission is generally safer than mono-polar energy applications which can create coagulation zones that are too deep. Also, the characteristics of each electrode 42, when such characteristics vary as described, may change. That is, the characteristics of the electrodes 42 may alternate or otherwise change with time during use of the medical instrument 40. Such varying signal characteristics, or multiplexing, results in higher levels of energy concentrated at and delivered from the electrodes 42 as a result of the interaction between the differing signals between the adjacent electrodes. The probe may have one or more traction elements 52. The traction element 52 may be a handle.

FIG. 4 shows a third embodiment of a medical device 50 according to the present invention that includes an endoscope 54. Although FIG. 4 shows one type of endoscope 54, any conventional type of endoscope may be used without departing from the scope of the present invention. The endoscope 54 may be a flexible endoscope, such as those commonly used in upper endoscopy examinations, or esophagogastroduodenoscopy (EGD). The endoscope 54 has an elongate primary body 56 and an elongate tubular portion 58 extending from the body 56 to a working end 62. The endoscope 54 also has a working channel 64 beginning at an entry orifice 66 on the primary body 56 and terminating at a terminal port 70 at the extreme end 68 of the shaft 58. The working channel of conventional endoscopes has a diameter, or minimum width if non-circular, of about three millimeters. In one embodiment of the present invention, the probe 12 and transparent tip 26 are sized and shaped for slidable receipt within the working channel 64 of the endoscope 54. The probe 12 and tip 26 of this embodiment are otherwise identical to the probe and tip of the earlier described embodiments, and therefore will not be described in further detail.

As shown in FIG. 5, the medical device 50 can have viewing optics 72 for viewing an object (not shown) positioned in a viewing area (not shown) adjacent the working end 62 of the endoscope 54. The viewing area includes all the objects visible through the viewing optics, including the tip 26, the electrodes 42, and adjacent tissue (not shown). Although the viewing area may have other shapes without departing from the scope of the present invention, in one embodiment the area is circular. The optics 72 are disposed within the endoscope 54, beginning at a location (not shown) near the primary body 56, where a user may receive images, and terminating near an optics orifice 73. Although the optics 72 may be located otherwise, in the embodiment shown it will be appreciated that the optics 72 are located on a side of the tip that is opposite of the side of the tip having the electrodes 42. The endoscope 54 further has an illuminator 75 for directing light toward the tip 26 and an object (not shown) positioned adjacent the working end 62 of the shaft 58. As with the optics 72, the illuminator 75 originates at a location (not shown) near the primary body 56 and terminates near the end 68 of the shaft 58.

A primary purpose for the ablation device is to ablate diseased esophageal tissue for combating Barrett's esophagus. Although the medical device is described as ablating abnormal esophageal mucosa, the device may ablate other tissues or things other than tissue without departing from the scope of the present invention.

In operation, a user of an ablation device 50 according to the present invention first positions the elongate probe 12 in the working channel 64 of the endoscope 54 so the transparent tip 26 connected to the probe 12 extends through the port 70 of the working channel 64 at the working end 68 of the endoscope. The electrodes 42 are connected to an energy source 18. The probe 12, tip 26, and energy source can be the same as any of the earlier described embodiments, and therefore will not be described in further detail. After positioning the ablation device 50 as described, the user moves the probe 12 to a desired location (not shown) within the patient (not shown), for example, by viewing at least one electrode 42 positioned on the surface of the tip 26 through the tip. The positioning may include articulating the shaft 58 of the endoscope 54, rotating the probe 12 with respect to the endoscope 54, and/or translating the probe 12 with respect to the endoscope 54. Once the medical device 40 has been positioned, the user can destroy the targeted tissue of the patient (not shown) located adjacent the electrode by energizing the electrode 42. By this local and accurate ablation method, diseased mucosal tissue is destroyed. A short period of time after the procedure, the destroyed tissue will be sloughed off (i.e., through the normal digestive process) and healthy mucosal tissue will grow in its place. The type of energizing may be of any conventional type, including the types mentioned above regarding energy source 18, such as radio frequency, electrical, and ultrasonic. Although the therapeutic method described was described with reference to medical device 50, it will be appreciated by those skilled in the art that the method can be performed in a substantially similar manner using any of the disclosed embodiments without departing from the scope of the present invention.

Although a preferred use of the medical device is to ablate tissue in a patient, the device may also be used on materials other than tissue. In view of the above, it will be seen that the several objects of the invention are achieved.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A medical device for performing a therapeutic procedure on a patient comprising:
    an elongate probe extending to an applicator end;
    a visually transparent tip including a lateral surface positioned adjacent the applicator end of the probe; and
    an electrode positioned on the lateral surface of the tip so that the electrode may be viewed through the tip, said electrode being communicative with an energy source for delivering energy to the electrode when performing the therapeutic procedure on the patient;
    wherein the probe and tip are sized and shaped to be slidably received in an endoscope working channel.

2. A medical device as set forth in claim 1 wherein the tip has a maximum width less than about three millimeters.

3. A medical device as set forth in claim 1 wherein said transparent tip is attached to the applicator end of the probe.

4. A medical device as set forth in claim 1 wherein the lateral surface is positioned on a first side of the tip, the tip includes a second side opposite the first side, and the second side is substantially free of electrodes.

5. A medical device as set forth in claim 4 wherein the tip includes a first end adjacent the probe and a second end opposite the first end, and the first and second sides taper toward each other from the first end of the tip to the second end.

6. A medical device as set forth in claim 5 wherein said first and second sides are separated by a third side and a fourth side opposite the third side, and the third and fourth sides taper toward each other from the first end of the tip to the second end.

7. A medical device as set forth in claim 4 wherein the tip magnifies images transmitted through the tip from the first side to the second side.

8. A medical device as set forth in claim 1 wherein said electrode is a first electrode and the device includes a plurality of electrodes including said first electrode positioned on the tip.

9. A medical device as set forth in claim 8 wherein each electrode of said plurality of electrodes is positioned on the lateral surface of the tip.

10. A medical device as set forth in claim 8 wherein the electrodes are communicative with a radio frequency source for selectively delivering radio frequency energy to the electrodes.

11. A medical device as set forth in claim 8 wherein the electrodes are communicative with an ultrasonic energy source for selectively delivering ultrasonic energy to the electrodes.

12. A medical device as set forth in claim 8 wherein the electrodes are communicative with an electrical source for selectively delivering electrical energy to the electrodes.

13. A medical device as set forth in claim 12 wherein, during operation of the device, adjacent electrodes of said plurality of electrodes are oppositely charged.

14. A medical device as set forth in claim 13 wherein, during operation of the device, the charge on each electrode changes with time.

15. A medical device for performing a therapeutic procedure on a patient comprising:
    an elongate endoscope extending to a working end, said endoscope including optics for viewing an object positioned in a viewing area adjacent the working end of the endoscope and having a working channel extending along the endoscope to a port adjacent the working end; and
    an elongate probe slidably received in the working channel of the endoscope, said probe including a visually transparent tip including a lateral surface positionable adjacent the working end of the endoscope and in the viewing area, and an electrode positioned on the lateral surface of the tip so that the electrode may be viewed through the optics of the endoscope when said tip is positioned adjacent the working end of the endoscope and in the viewing area, said electrode being communicative with an energy source for delivering energy to the electrode when performing the therapeutic procedure on the patient.

16. A medical device as set forth in claim 15 wherein the endoscope further comprises an illuminator for directing light toward an object positioned adjacent the working end.

17. A medical device as set forth in claim 15 wherein the tip magnifies images transmitted through the tip.

18. A method for performing a procedure on a patient, said method comprising:
    positioning an elongate probe in a working channel of an endoscope so a visually transparent tip connected to the probe having an electrode positioned on a first lateral surface of the tip extends beyond a port at a working end of the endoscope;
    viewing the positioned on the first lateral surface through a second lateral surface of the tip that is opposite the first lateral surface using the endoscope;
    moving the probe so the electrode is at a desired location within the patient; and
    energizing the electrode to remove from the patient tissue positioned adjacent the electrode.

19. A method for performing a procedure as set forth in claim 18 wherein the step of moving includes at least one of articulating the endoscope, rotating the probe with respect to the endoscope and translating the probe with respect to the endoscope.

20. A method for performing a procedure as set forth in claim 18 wherein the tip magnifies images transmitted through the tip from the first lateral surface of the tip to the second surface of the tip and the viewing step includes viewing the electrode in magnification.

* * * * *